United States Patent [19]
Barrick et al.

[11] Patent Number: 5,266,499
[45] Date of Patent: Nov. 30, 1993

[54] METHOD FOR DETECTION OF ANTIBODIES FOR METALLIC ELEMENTS

[75] Inventors: Charles W. Barrick, Golden; Sara M. Clarke, Larkspur; Carl W. Nordin, Golden, all of Colo.

[73] Assignee: The United States of America as represented by the United States Department of Energy, Washington, D.C.

[21] Appl. No.: 856,105

[22] Filed: Feb. 25, 1992

Related U.S. Application Data

[62] Division of Ser. No. 473,792, Feb. 2, 1990.

[51] Int. Cl.$^5$ .......................................... G01N 33/553
[52] U.S. Cl. .................................. 436/525; 436/518; 436/809; 436/810; 422/57
[58] Field of Search ................ 436/809, 810, 518, 525

[56] References Cited
PUBLICATIONS

Clarke–J. Immunol. Methods vol. 137 (1991) pp. 65–72.
Sterner et al–Industrial Hygiene & Occupational Medicine vol. 4 (1951) pp. 123–151.

*Primary Examiner*—Sam Rosen
*Attorney, Agent, or Firm*—Armand McMillan; James H. Chafin; William R. Moser

[57] ABSTRACT

An apparatus and method for detecting antibodies specific to non-protein antigens. The apparatus is an immunological plate containing a plurality of plastic projections coated with a non-protein material. Assays utilizing the plate are capable of stabilizing the non-protein antigens with detection levels for antibodies specific to the antigens on a nanogram level. A screening assay with the apparatus allows for early detection of exposure to non-protein materials. Specifically metallic elements are detected.

4 Claims, 10 Drawing Sheets

| Plasma Dilutions | Sample #1 | | | Sample #2 | | | Sample #3 | | | Sample #4 | | | Pooled Control | | Buffer Control | |
|---|---|---|---|---|---|---|---|---|---|---|---|---|---|---|---|---|
| 1:2 | | | | | | | | | | | | | | | | |
| 1:4 | | | | | | | | | | | | | | | | |
| 1:8 | | | | | | | | | | | | | | | | |
| 1:16 | | | | | | | | | | | | | | | | |
| 1:32 | | | | | | | | | | | | | | | | |
| 1:64 | | | | | | | | | | | | | | | | |
| 1:128 | | | | | | | | | | | | | | | | |
| 1:256 | | | | | | | | | | | | | | | | |

METHOD FOR DETECTION OF ANTIBODIES FOR METALLIC ELEMENTS

The government has rights in this invention pursuant to contract number DE-AC04 76DP03533 awarded by the U.S. Department of Energy.

This is a division of application Ser. No. 07/473,792 filed Feb. 2, 1990.

BACKGROUND OF THE INVENTION

The present invention relates generally to antibody detection assays, and more particularly to a method and apparatus for an antibody detection assay for non-protein immunological studies comprising an immunological plate coated with non-protein antigen.

The field of immunology is generally concerned with antigens of biological molecules, primarily proteins and their corresponding antibodies (IgG). Recently, reports have been published on the existence of antibodies to other types of molecules, and more specifically to inorganic chemicals. However, no reports have been published on the existence of IgG molecules specific to non-protein substances such as elemental oxides, inorganic substances, metals and the like.

The existing technology for antibodies study is designed for protein (antigen) attachment, by adsorption, onto specially coated plastics. With organic molecules, the method currently being used to study antibodies to organic molecules is to attach a protein, usually albumin, to the organic molecule to form hapten. The hapten is then attached to the specially coated plastics. However, the study of antibodies to non-protein materials is difficult due to the lack of a method to attach these antigens to a stable base.

Antibodies are normally produced by the immune system about 14 days after internal exposure to a foreign substance. After the foreign substance has been eliminated, the antibody titer (amount) diminishes. If the foreign substance remains in the system, the antibody titer will remain high. Thus, assays allow the presence of a foreign substance to be monitored.

The need for detecting antibodies for non-protein substances is great. For example, it is known that the inhalation and deposition of microscopic particles of beryllium in the lungs can cause an incurable lung illness called chronic beryllium disease (berylliosis). This disease usually takes many years to evolve. Thus, it is desirable to design and develop a test which would indicate when a person has been internally exposed to beryllium. Such a test would provide sufficient opportunity to intervene and perhaps prevent maturation of the disease.

There are many reported increases in the immunoglobulin levels of patients with chronic beryllium disease (P.T. Pugliese 1968; H. Resnick et al 1970, S.D. Deodhar et al 1973, E.V. Vasilyeva et al 1977). In certain areas of Czechoslovakia, where coal with a high beryllium content is burned, high levels of immunoglobulins have been found in the workers and the general public (Bencko, et al 1980). Also, it has been demonstrated in vitro that beryllium sulphate causes a mitogenic effect on mouse B lymphocytes cells which produce antibodies (L.S. Newman and P.A. Campbell, 1987).

Sterner and Eisenbud, in their 1951 paper "Epidemiology of Beryllium Intoxication," state that the pathogenesis of berylliosis may be based on a concept that beryllium combines with protein to form an antigen, which in turn stimulates a beryllium-specific antibody. An inflamation results from the subsequent reaction of beryllium and the specific antibody. Even though attempts have been made to locate a beryllium specific antibody, none have been found.

Thus, there is a need for detecting exposure to non-protein materials so that appropriate action can be taken to prevent disease.

SUMMARY OF THE INVENTION

The present invention provides an apparatus and method for detecting the presence of antibodies specific to non-protein substances. According to a feature of the present invention, immunological plates are coated with a non-protein material, such as an inorganic material, so that detection of antibodies specific to the material can be made. Antibodies specific to the particular material can be found through assays with the coated immunological plates.

The invention may use molecular deposition to stabilize non-protein antigens on a substrate allowing for very sensitive detection methods (on nanogram levels) for detecting antibodies specific to the antigens. Thus, the invention allows for an antibody screening assay which permits early detection of non-protein material before disease occurs.

DETAILED DESCRIPTION OF PREFERRED EMBODIMENTS

The invention provides an apparatus and method for detecting the presence of antibodies specific to non-protein antigens. In general, immunological plates designed for protein adsorption are adapted for non-protein immunological studies. The immunological plates are coated with a non-protein antigen using a molecular deposition technique.

Commercially available immunological plates may be used in the present invention. A number of commercially available plates are known. For example, FALCON Assay Screening Test (F.A.S.T.) plates, available from Becton Dickenson or Nunc Transferable Solid Phase (Nunc TSP) immunological microstick plates may be utilized in the present invention. These plates generally comprise a plurality of plastic (for example, polystyrene) projections or pins designed for adsorption of antibodies for sensitive measurements. Of course, any substrate can be used and coated, provided that the coated antigen remains on the substrate during an assay.

Figure 1:
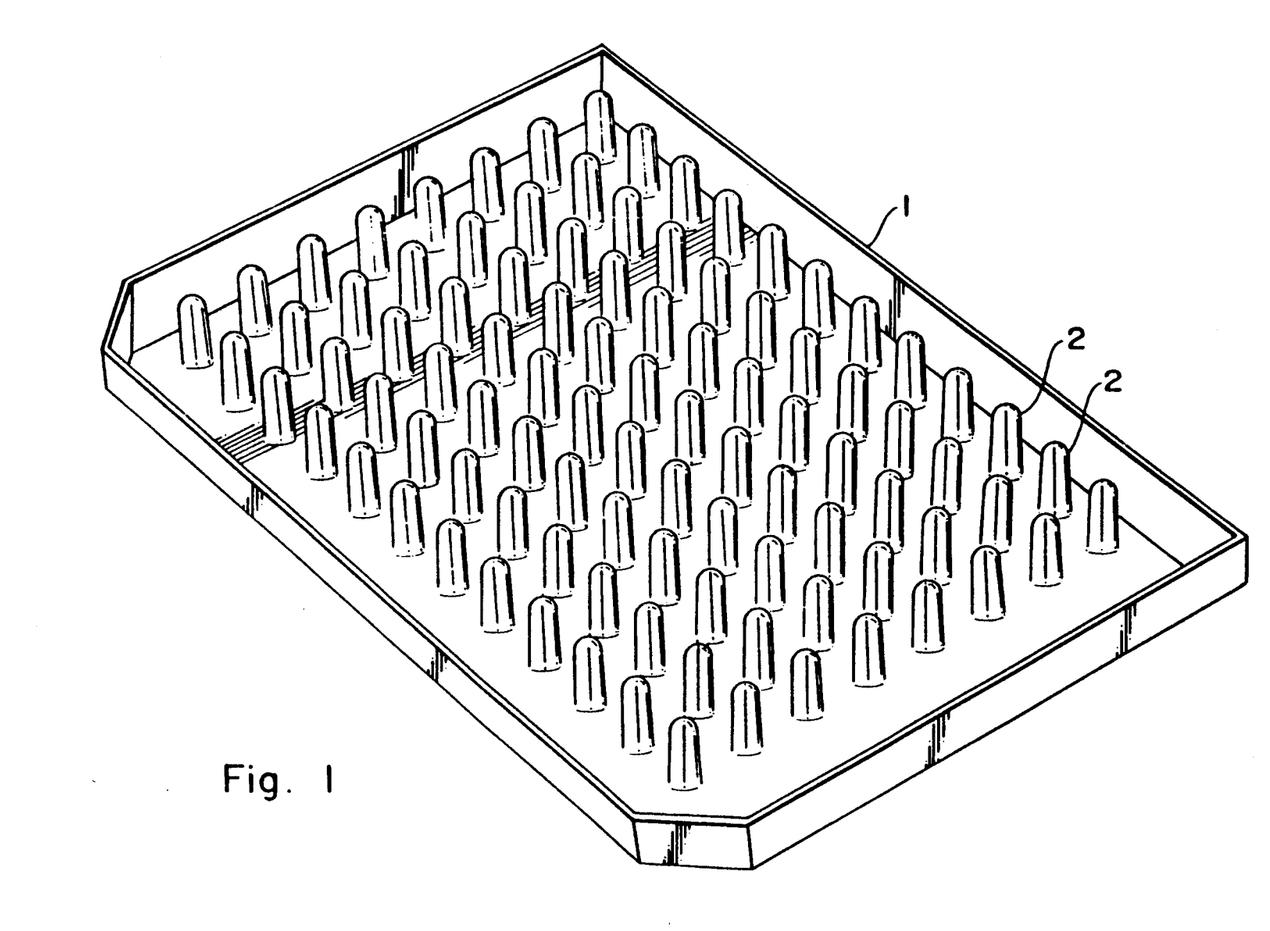
FIG. 1 is a schematic representation of an immunological plate used in the invention.

Referring to FIG. 1, an immunological plate 1 of the invention is shown. The plate has a plurality of projections 2 arranged in columns and rows. A corresponding solution plate may be provided with containers or troughs for holding sample solutions. In these plates, the projections 2 are coated with a single concentration of non-protein antigen which is used to capture a particular antibody.

In the present invention, conventional immunological plates are coated with a non-protein antigen. For example, the plates can be coated with an inorganic material such as elemental oxides, inorganic substances, metals and the like. More specifically, the plates can be coated with metals such as beryllium, gold, vanadium, aluminum, silicon, nickel, chromium, and any other desirable materials.

The immunological plates may be coated using a molecular deposition process which will stabilize the non-protein antigens. Coating of the plate may be done by vacuum deposition, for example, hot filament evaporation, variable sputtering techniques, electron beam evaporation, and the like. Coatings having a thickness of about 1000 Anstroms to about 2000 Angstroms may be used, and coatings having a thickness of about 1000 Angstroms to about 1500 Angstroms are preferred. Very sensitive detection methods on the nanogram level are possible with the coated plates,, allowing detection of the presence of antibodies specific to these substances. As many non-protein substances such as metals are being implicated in chronic lung diseases, specific antibodies of these non-protein substances may be detected.

Figure 2A:
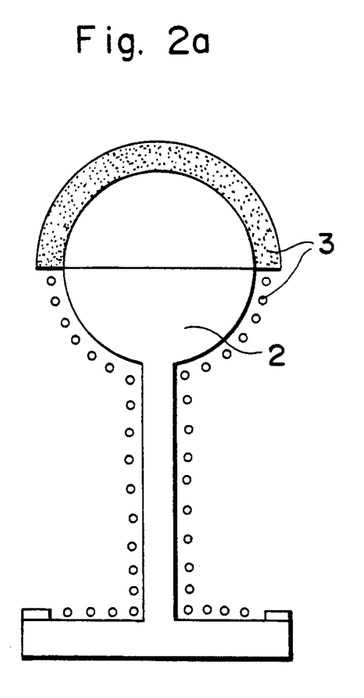
FIGS. 2(a) and 2(b) show coated projections of the immunological plates of the invention.
Figure 2B:
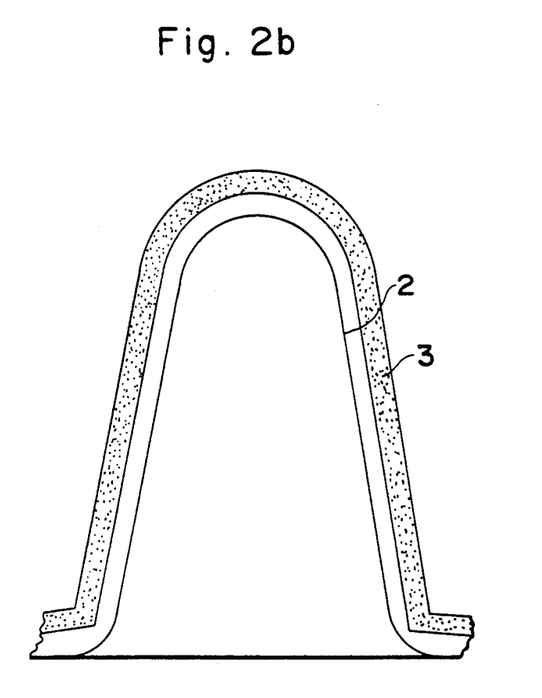

With some immunological plates, it may be difficult to obtain a complete uniform layer thickness of the coating. This is most often seen on plates with projections having spheres at their ends. For example, FIGS. 2(a) and 2(b) show coated projections on Nunc TSP and F.A.S.T. plates. The Nunc TSP projection (pin) is slightly sloping, as shown in FIG. 2(b), which allows for a uniform coating 3 over the entire surface of the projection 2. The coating 3 of the spherical projection 2 may not be as complete and uniform due to shadowing effects from the spheres as illustrated in FIG. 2(a). However, the projections need only be sufficiently coated with non-protein antigen at their ends to permit detection of antibodies.

Coatings of non-protein materials, such as metals, are opaque and reflective. Thus, coating quality can be optically inspected for uniformity and thickness both before and after use. Plate inspection before use permits rapid detection of antigen coating variables. Plate inspection after use permits rapid detection of gross loss and adverse reaction of the antigen coatings. Further, the molecular deposition coated plates offer a unique advantage for antigen-antibody surface characterization.

The non-protein coated immunological plates of the present invention can be used in assaying methods similar with those used with known protein assaying methods. For example, in an assaying method, a trough is provided for holding a solution of antigen. The trough is filled with a soluble antigen. A separate trough or row may be used as a positive or negative control. A plate containing a plurality of projections is placed in the trough containing antigen and incubated long enough to achieve sufficient antigen adsorption. The projections are then washed with phosphate buffered saline (PBS). The plate is placed in a second trough containing solution to block the remaining sites on the projection,, which produce non-specific binding of antibodies in future steps. After incubation, the projections are rinsed with PBS and placed onto a 96 well plate filled with the test solution which may contain the screened for antibody. If this antibody is present, it will recognize and bind to the antigen for which it is specific. The plate covered with the projections is then incubated. The projections are removed, rinsed with PBS, and placed in a trough containing a secondary, enzyme-labeled antibody. This antibody helps specifically identify which projections possess primary antibody. Then, the projections are washed and placed in the assay plate that has been filled with a chromogenic substrate solution. A color reaction will occur in the positive wells. This reaction can be assessed visually for each well, which can be quantified by using a spectrophotometer, and the optical density (OD) readings can be compared to standard curves. In the present invention, antibodies specific to the non-protein antigens which attach to the antigen coated projections and may be detected by a color reaction with a chromogenic substrate solution.

The invention will be further illustrated by reference to the following non-limiting examples. The examples are provided merely to illustrate the invention, and are not intended to limit the scope of the invention.

EXAMPLE 1

Plates having 96 plastic spheres (F.A.S.T. plates, from Becton Dickenson) are coated with various metals. The plates typically are 5.0 inches by 3.5 inches. The spheres are about 0.125 inch in diameter and are equally spaced over the surface of the plates, and are positioned off one large surface of the plate on 0.250 inch posts. The posts have a diameter less than that of the diameter of the spheres (about 0.065 inch).

A plate is coated by electron beam evaporation with beryllium in a beryllium chamber. A total of 18 runs are made using beryllium as the evaporant. The first two runs are made with the plate 9.875 inches over the center of the electron beam evaporation source. The second set of plates is coated by placing them 7 inches of f of the vertical axis of the chamber, and are mounted in a holder 10.25 inches above the electron beam source. The plates are rotated over the center of the chamber to give a good distribution over all the spheres. The deposition power is 10 kv-60 mils for a one minute run at room temperature for all runs. Adherence of the beryllium to the plastic spheres is excellent. The distribution is not uniform when the plates are coated in a position over the center of the source. When coated in a position of f the axis of the chamber, the distribution is excellent.

Plates are coated with gold in an all general purpose coating system. Evaporation is from a filament heated tungsten boat. After bringing the gold to melting point, the filament is then flashed for about one minute to ensure that all of the gold has been evaporated. The distance from the source to the substrate is 6 inches. The adherence of gold to the plastic spheres is excellent, but some shadowing from the spheres is observed on the back of the spheres.

Plates are also coated with vanadium in a general purpose coating system. The coating runs are made over the center of the electron beam evaporation source. The distance is 6 inches from the electron beam evaporation source to the plates. Deposition power is 10 kv-20 mils for a 10 second run. The adherence of the vanadium to the plastic spheres is excellent. Some shadowing is observed on the back of the spheres.

EXAMPLE 2

Nunc TSP immunological microstick plates are coated with a thin opaque layer of beryllium using an electron beam evaporation source. The plates are rotated over the center of the vacuum chamber. Deposition power is 10 kv-60 mils for one minute at room temperature. The beryllium coated plates are stored at room temperature in a dessicator until used. Test and control plates are rinsed three times with phosphate buffered saline (PBS), pH 7.3, and then incubated for one hour in 1% normal goat serum on a rotating surface at 23° C. Beryllium-coated plates represent the "test plate" and non-coated plates represent the "control plate".

Figure 3:
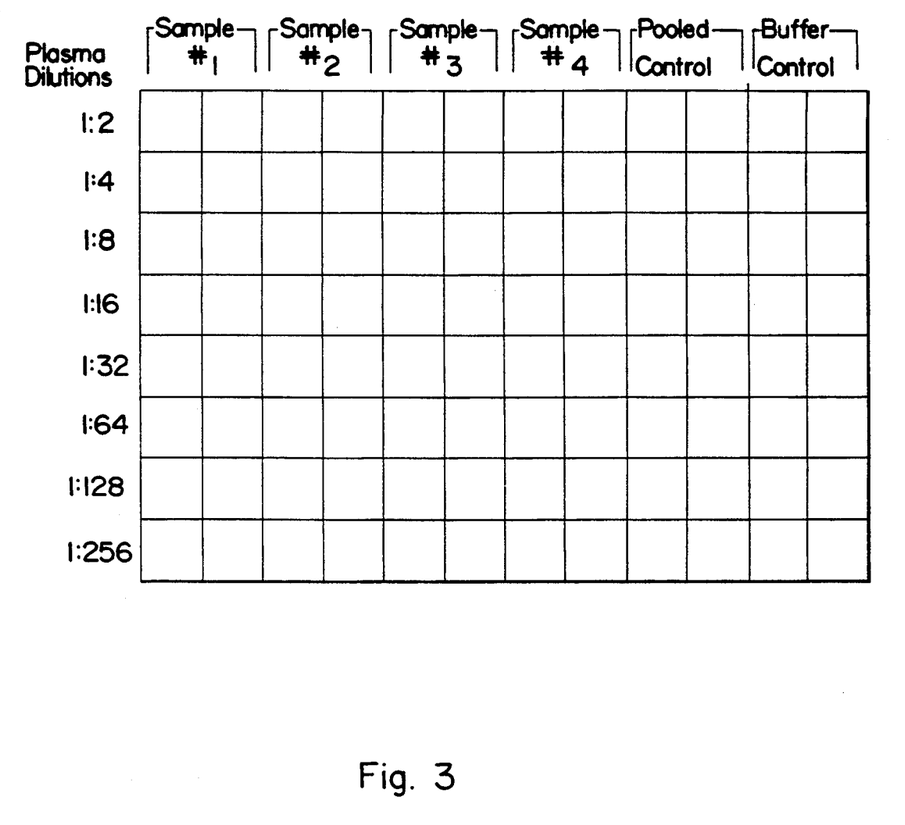
FIG. 3 shows an arrangement and dilutions of samples in an immunological plate of the invention.

Plasma from beryllium exposed and non-exposed workers is serially diluted in PBS from 1:2 to 1:256 as shown in FIG. 3. Duplicate aliquots (200 microliters) of the samples are placed in 96 well control and test plates. The rinsed and blocked test and control microsticks are placed into plasma samples and rotated for one hour at 23° C. After rinsing the microsticks three times in 96 individual wells to prevent translocation of the plasma proteins, the antigen-antibody complexes located on the microsticks are detected by an amplification method using a biotinylated anti-antibody and an avidin-peroxidase conjugate (ABC Vectastain, Vector Labs Burlingame, Calif.). Incubation in each of these reagents was for 45 minutes on a rotating surface at 23° C. A 0.1 mg/ml solution of ABTS (2,2'-azinobis-3-ethylbenzthiazoline sulfonic acid) in 50 mM citrate/phosphate buffer, pH 5.3, and 0.015% hydrogen peroxide, is used as the peroxidase substrate. Incubation in the substrate is for 25 minutes in the dark at room temperature. Wells are read in a MR700 Dynatek spectrophotometer using a 410 nm test filter and a 450 rm reference filter. The instrument is blanked on the substrate. Control plate readings are subtracted from the test plate readings and the resulting optical density (OD) units are graphed versus the reciprocal of the plasma dilutions.

Scanning electron microscopic (SEM) analyses of the beryllium coated Nunc TSP microsticks reveal a smooth, even dispersion of beryllium without oil or dirt contamination. Wipes taken on the surf ace of the microsticks and analyzed for beryllium by a neutron activation method using an antimony source show excellent adherence as no beryllium is found.

Figure 4:
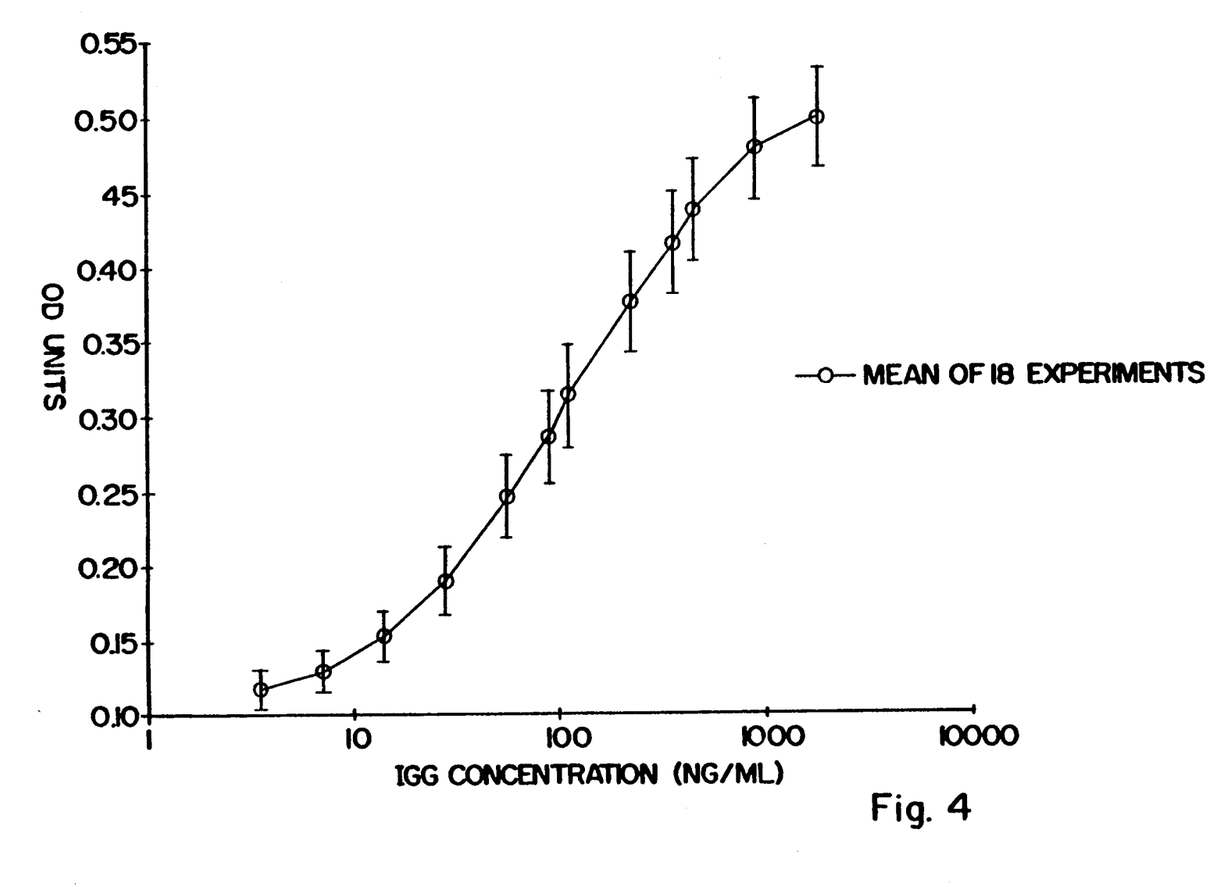
FIG. 4 is a graph of a human IgG standard curve.

A standard curve is established using known concentrations of human antibodies (IgG). Testing the curve showed the assay to be reproducible and sensitive to the nanogram ($10^{-9}$) level, as shown in FIG. 4.

Figure 5:
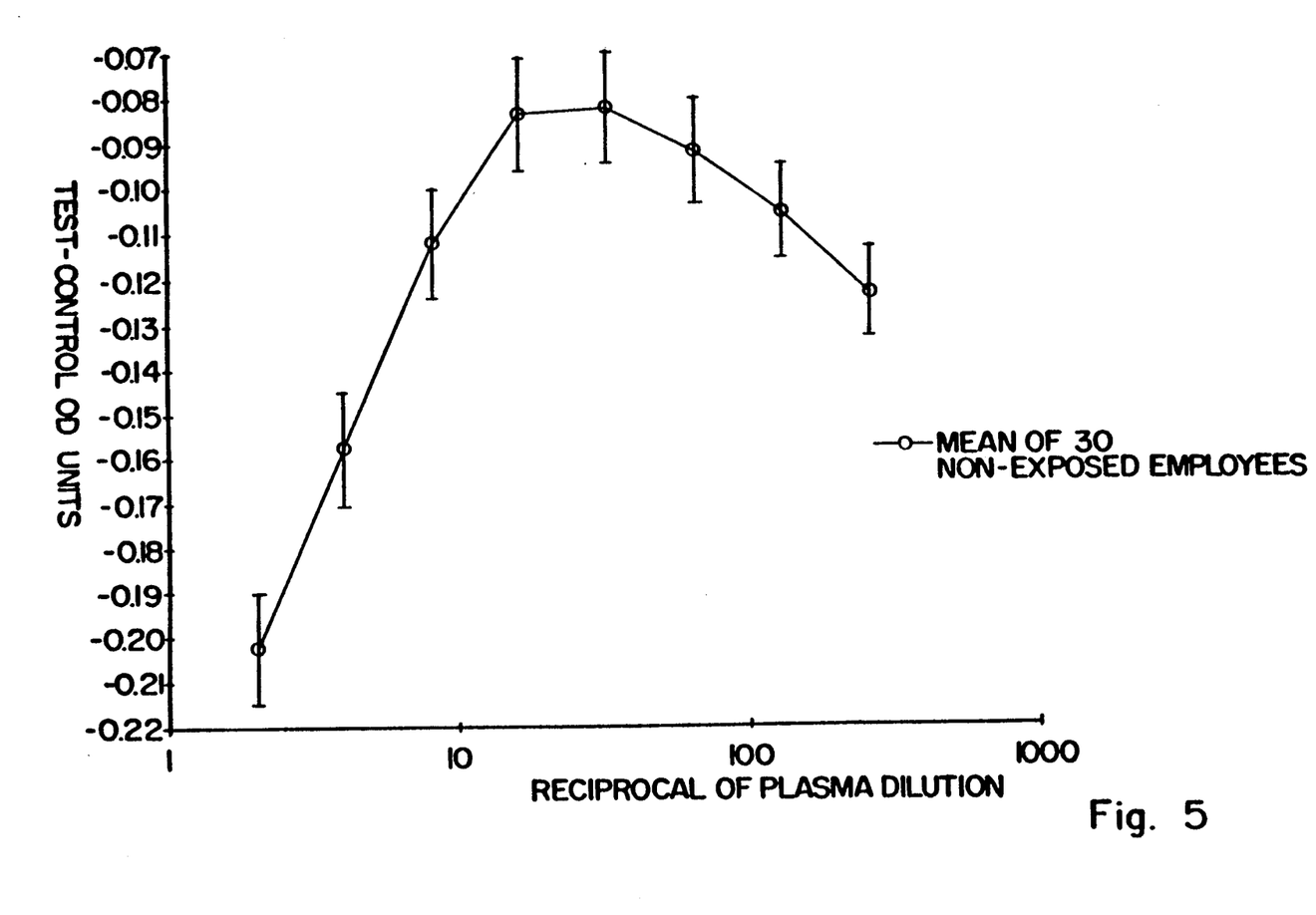
FIG. 5 is a graph of beryllium antibody titers of non-exposed workers.

Blood is drawn from 30 Rocky Flats Plant. (RFP) employees with no known beryllium exposure. The plasma from these samples is pooled and run in the assay. FIG. 5 shows the results.

Figure 6:
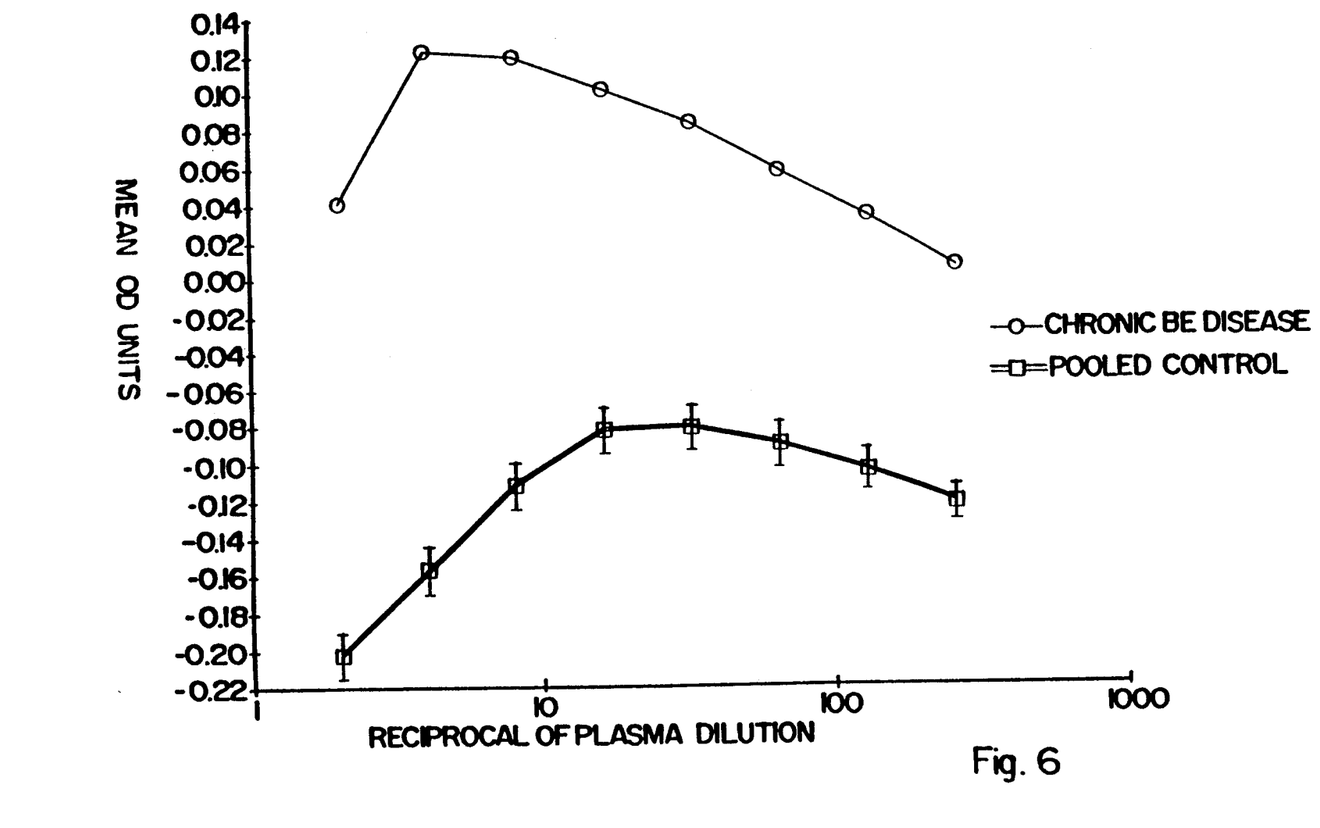
FIG. 6 is a graph of a beryllium antibody screening assay.

Blood from a RFP employee diagnosed with chronic beryllium, disease is tested in the assay. Two experiments are averaged and compared to the pooled normal control. FIG. 6 shows that the employee with chronic beryllium disease has a higher beryllium antibody titer than the control.

EXAMPLE 3

Figure 7:
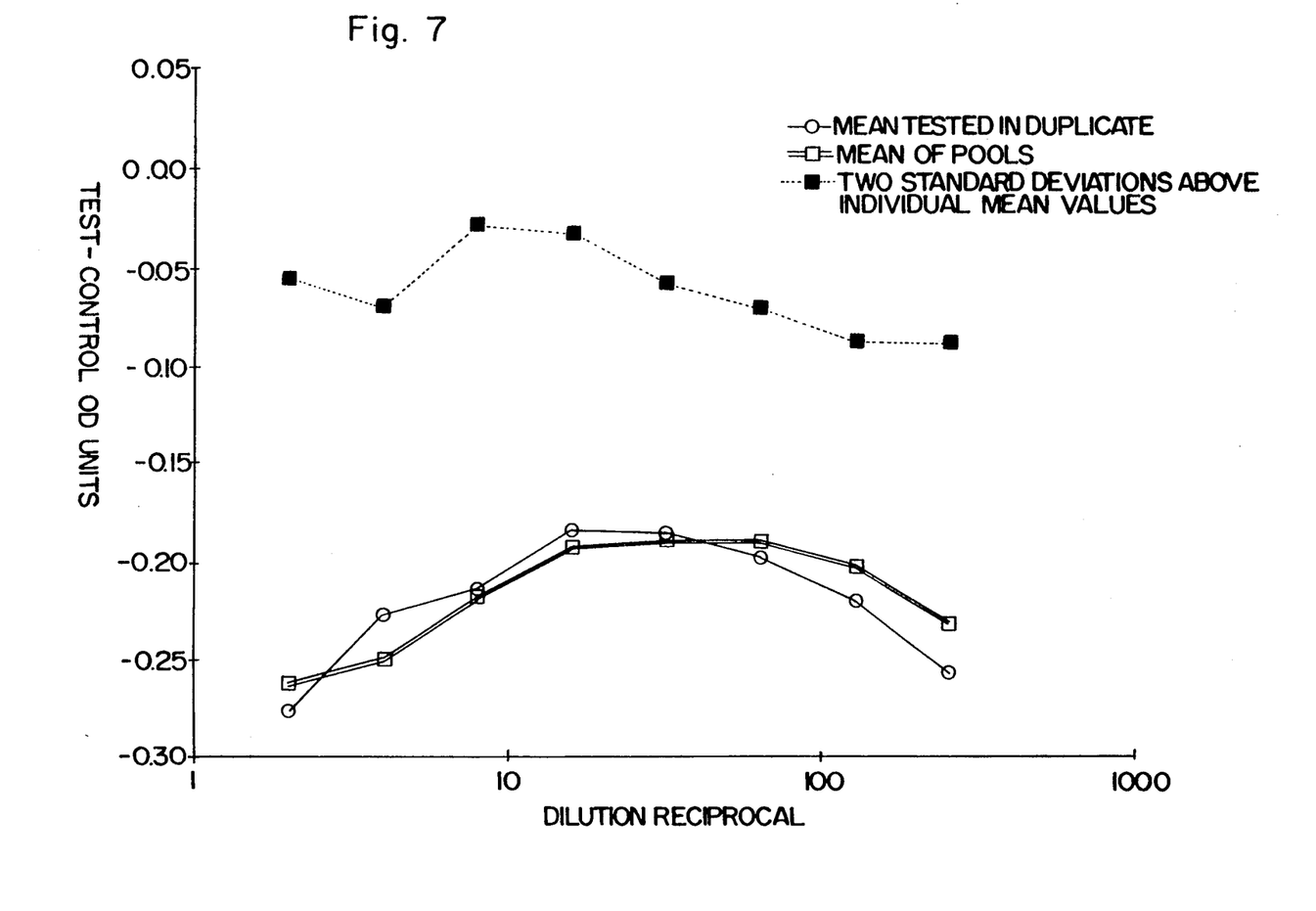
FIG. 7 is a graph of baseline control population samples tested in the beryllium antibody assay of the present invention.

Nunc TSP immunological microstick plates are prepared in accordance with the procedures set forth in Examples 1 and 2. To determine the beryllium antibody level in the base line control population, blood from 12 summer students and 12 new hirers is used. Each volunteer is tested separately and in pools of four. The average titer of the 24 separate tests is compared to the average of the six pools of four. No significant differences are found. Two standard deviations are calculated from the duplicate readings of the 24 individual assays in all eight dilutions and are used as the upper cut off value for the baseline population as shown in FIG. 7.

Validation of the beryllium antibody response is shown by three different approaches; reproducibility, inhibition by removal of antibodies, and the use of an affinity purified gamma chain specific biotinylated anti IgG reagent.

Reproducibility of the assay is tested by drawing random duplicate blood samples from 15 workers. The duplicates are assayed and no significant differences in any of the paired curves are found.

Figure 8:
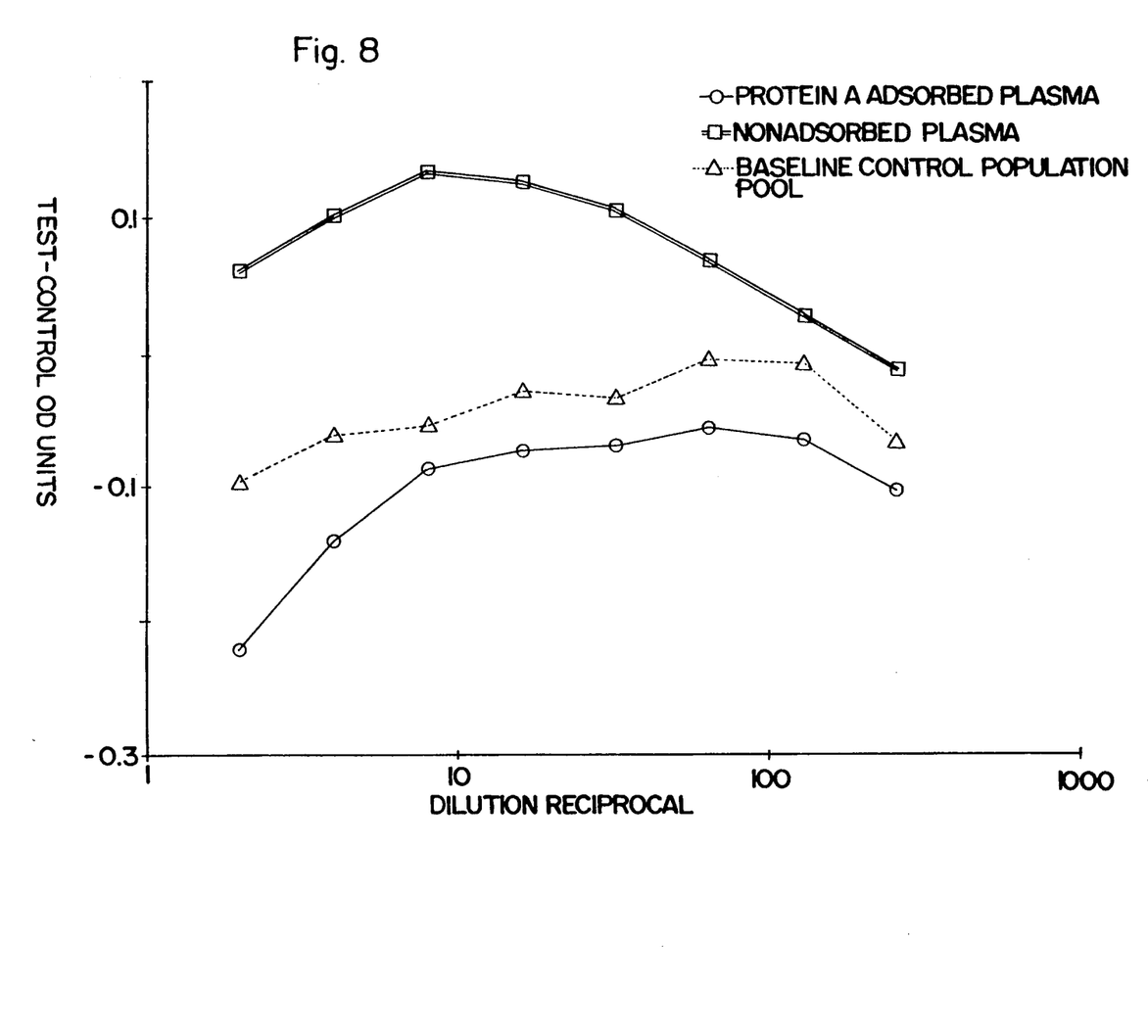
FIG. 8 is a graph of a beryllium antibody assay run on Protein A adsorbed plasma and nonadsorbed plasma.
Figure 9:
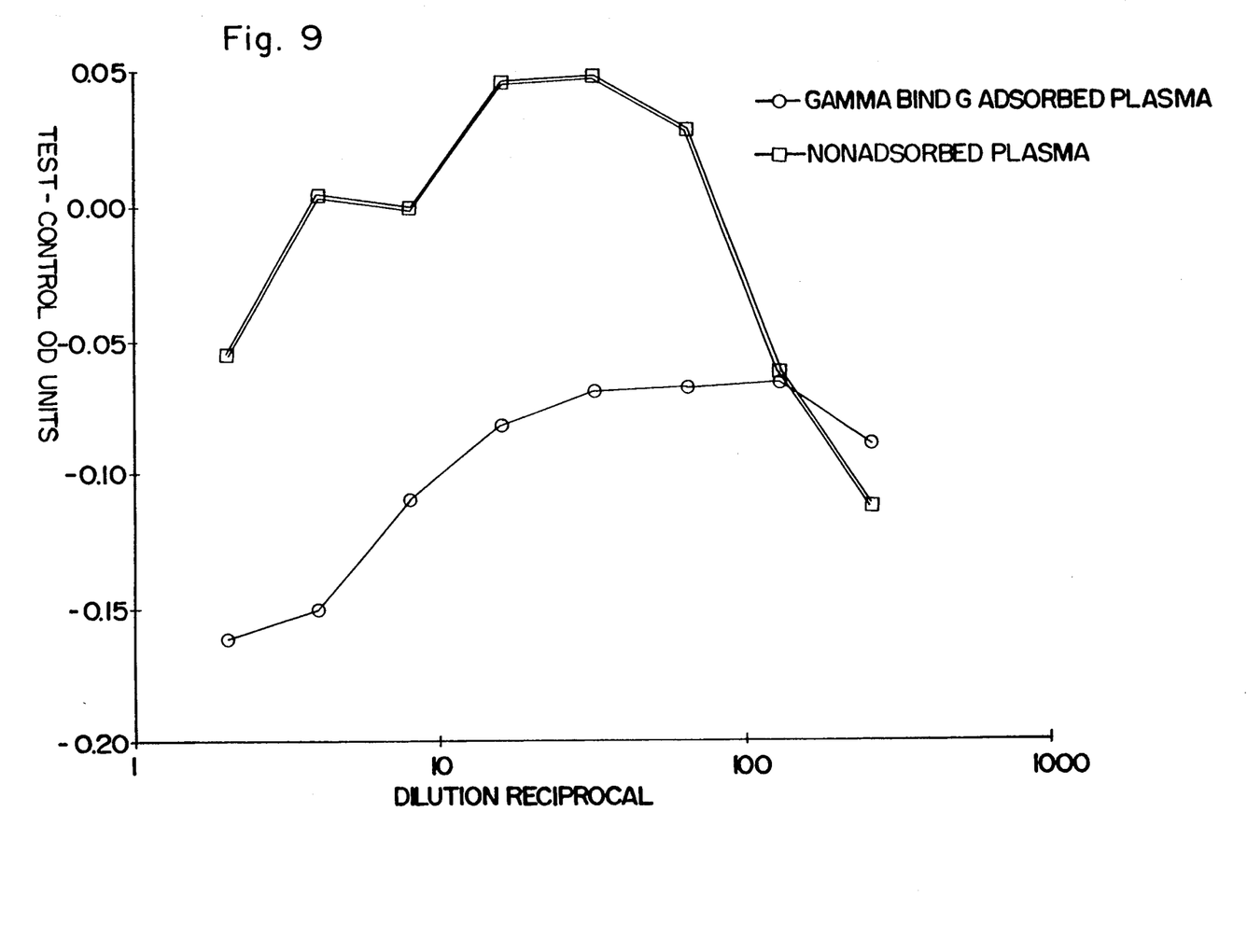
FIG. 9 is a graph of beryllium antibody assay run on GammaBind G adsorbed plasma and nonadsorbed plasma from a worker with chronic beryllium disease.

Protein A, which binds antibodies, is mixed with plasma from two workers, one of whom was sensitized to beryllium and one who was diagnosed with chronic beryllium disease. Both workers exhibit beryllium antibody levels above the base line control population plus two standard deviations. After mixture with protein A; the antibody titer falls to base population levels as shown in FIG. 8. The same phenomenon occurs when the plasma is mixed with GammaBind G. a protein made specifically to bind IgG molecules as shown in FIG. 9.

Figure 10:
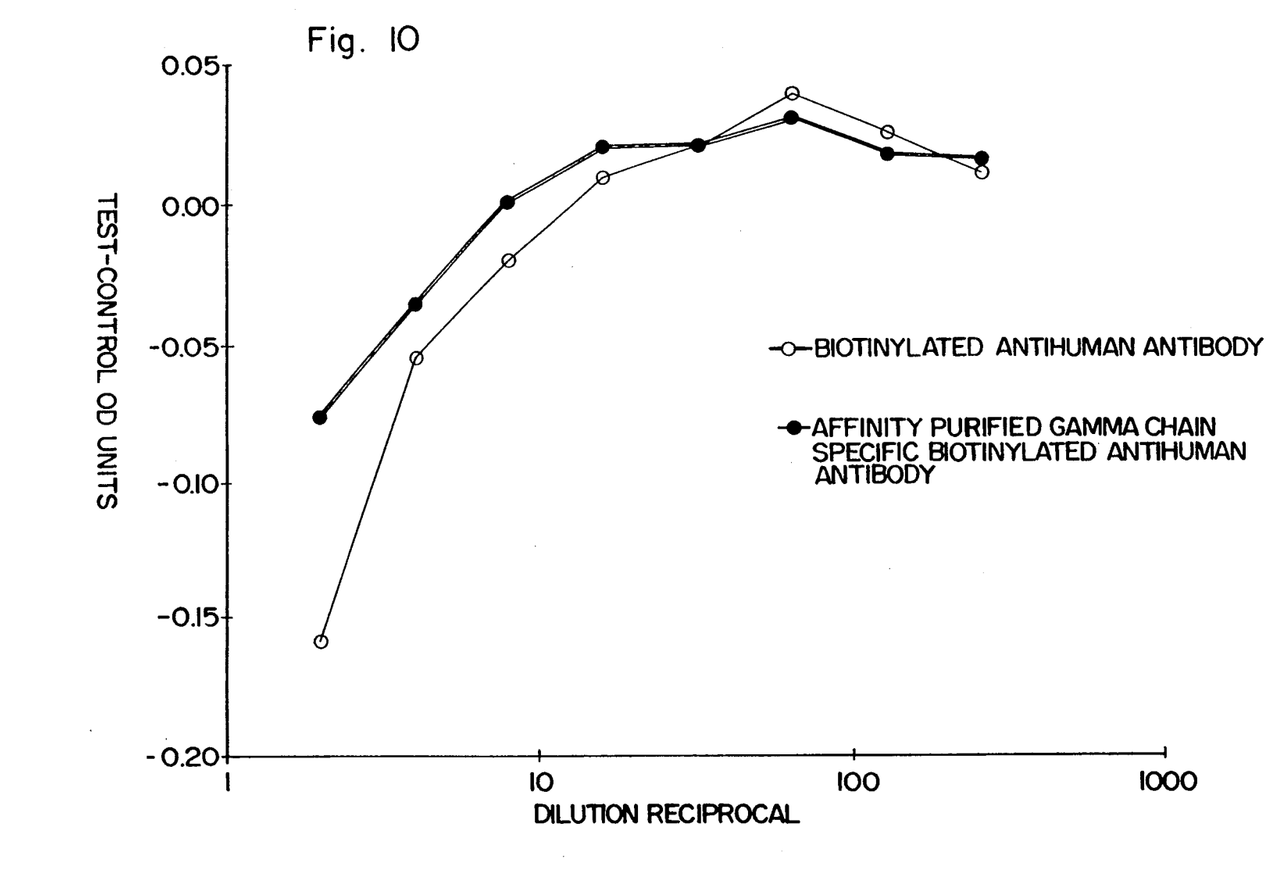
FIG. 10 is a graph showing a comparison of biotinylated antihuman antibody and affinity purified gamma chain specific biotinylated antihuman antibody.

The final validation test is done by substituting affinity purified "gamma chain specific" biotinylated antihuman antibody in the assay in place of biotinylated antihuman IgG and running the assay. The almost identical curves as shown in FIG. 10 indicate that this reaction is due to a human IgG molecule bound to beryllium or its oxide form.

The assay is used to screen 182 workers for beryllium antibodies. Forty-four samples are identified as having beryllium antibody levels above the base line control population plus two standard deviations in at least one of the eight plasma dilutions tested. An analysis of variance shows these 44 samples to be significantly different ($p > 0.001$) and higher than the control pool. Job histories reveal that 37 of the 39 positive workers (duplicate samples were taken on 5) have or had jobs where beryllium was present. The other two may represent the 2 ½ percent of the normal population which can be above the two standard deviations at each dilution.

EXAMPLE 4

Two methods of antigen (Be) attachment to immunological plates are compared; the negative charged method produced by exposing immunological (polystyrene) plates to an oxidizing atmosphere (Becton Dickinson) and the vacuum deposition of Be onto the plates. Both methods are capable of coating the immunological plate sticks with beryllium while the vacuum deposition method allows for greater reproducibility, sensitivity and coating verification.

A scanning electron microscope (SEM) study is performed on a plate that had been coated with Be using vacuum deposition to determine the extent of coating, the type of surface generated in the presence, if any, of contaminate. An even coating of beryllium with good attachment and no oil contamination is achieved.

There is evidence that non-specific antibodies are present at various levels in certain individuals. These non-specific antibodies produce a high background which may cause false negatives. Background interference is decreased by inserting an extra washing step, using 0.9% NaCl for the washing agent with 1% purified bovine serum albumin (BSA). When BSA is used as the blocking agent, a decrease in both the test plate and the control plate readings are seen.

While the present invention has been described with reference to particular preferred embodiments, the invention is not limited to the specific examples given, and other embodiments and modifications can be made by those skilled in the art without departing from the spirit and scope of the invention.

What is claimed is:

1. A method for detecting the presence of an antibody specific to a metallic element, comprising:
    coating the element onto an immunological plate having a plurality of projections;
    exposing said coated plate to a sample containing an antibody specific to said element so that said element binds with said antibody forming an antigen-antibody complex; and
    detecting said antigen-antibody complex.

2. The method of claim 1, wherein said element is selected from the group consisting of beryllium, gold, vanadium, aluminum, silicon, nickel, and chromium.

3. The method of claim 1, wherein said antigen-antibody complex is detected by an amplification method using a biotinylated anti-antibody and an avidin-peroxidase conjugate.

4. The method of claim 1, wherein said plate is exposed by incubation.

* * * * *

UNITED STATES PATENT AND TRADEMARK OFFICE
CERTIFICATE OF CORRECTION

PATENT NO. : 5,266,499
DATED : November 30, 1993
INVENTOR(S) : Charles W. Barrick, et. al.

It is certified that error appears in the above-indentified patent and that said Letters Patent is hereby corrected as shown below:

On the Title page, item [75], inventor: should read-- Sara M. Clarke, Larkspur, Colorado--.

Signed and Sealed this

Ninth Day of August, 1994

Attest:

BRUCE LEHMAN

Attesting Officer

Commissioner of Patents and Trademarks